(12) United States Patent
Wang et al.

(10) Patent No.: US 8,759,073 B2
(45) Date of Patent: Jun. 24, 2014

(54) METHOD FOR EFFECTIVELY CONTROLLING HARMFUL ORGANISMS IN LARGE-SCALE CULTURE OF MICROALGAE

(75) Inventors: Huiling Wang, Hebei (CN); Weijing Ma, Hebei (CN); Xinxin Ma, Hebei (CN); Minsheng Liu, Hebei (CN)

(73) Assignee: ENN Science & Technology Development Co., Ltd. (CN)

( * ) Notice: Subject to any disclaimer, the term of this patent is extended or adjusted under 35 U.S.C. 154(b) by 358 days.

(21) Appl. No.: 13/386,895

(22) PCT Filed: Jul. 26, 2010

(86) PCT No.: PCT/CN2010/001135
§ 371 (c)(1),
(2), (4) Date: Apr. 6, 2012

(87) PCT Pub. No.: WO2011/009296
PCT Pub. Date: Jan. 27, 2011

(65) Prior Publication Data
US 2012/0184021 A1 Jul. 19, 2012

(30) Foreign Application Priority Data
Jul. 24, 2009 (CN) .......................... 2009 1 0089608

(51) Int. Cl.
*C12N 1/12* (2006.01)
(52) U.S. Cl.
USPC ...................................................... 435/257.1
(58) Field of Classification Search
USPC ...................................................... 435/257.1
See application file for complete search history.

(56) References Cited

U.S. PATENT DOCUMENTS 3,444,647 A * 5/1969 Takahashi .................... 47/1.4

FOREIGN PATENT DOCUMENTS

| CN | 1218830 A | 6/1999 |
| CN | 1544612 A | 11/2004 |
| CN | 101684447 A | 3/2012 |

OTHER PUBLICATIONS

Wang, X.Y.et al. Inhibition of ciliates by acidified alga *Chlorella vulgaris* fluid. Fisheries Science. Jul. 2005, vol. 24, No. 7,pp. 20-22, ISSN 1003-1111.
Lincoln, E.P.et al. Zooplankton control in mass algal cultures. Aquaculture. May 1983, vol. 32, Nos. 3-4, pp. 331-337, ISSN 0044-8486.
Liu Zhigang et al. Studies on Killing *Euplotes* Sp. and *Oxyrrhis* Sp. in the Culture Liquid of Marine Unicellular Alge. Journal of Zhanjiang Fisheries College, Dec. 1990, vol. 10, No. 2, pp. 36-41 (English Abstract).
1st Office Action dated Mar. 16, 2011 for the corresponding Chinese Application No. 200910089608.5 issued by SIPO and English translation of the Office Action.
2nd Office Action dated Feb. 29, 2012 for the corresponding Chinese Application No. 200910089608.5 issued by SIPO and English translation of the Office Action.

* cited by examiner

*Primary Examiner* — Jon P Weber
*Assistant Examiner* — Kailash C Srivastava
(74) *Attorney, Agent, or Firm* — Jack Schwartz & Associates, PLLC

(57) ABSTRACT

A method for effectively controlling harmful organisms in the large-scale culture of microalgae comprises the following steps:
(1) determining the harmful organism species causing contamination to the microalgae in culture, and the acid and alkali tolerance levels of said harmful organism species; and
(2) adjusting the pH value of the microalgae culture system according to the different acid and alkali tolerance levels of the harmful organisms; when the harmful organisms are determined to be killed or inhibited effectively, adjusting the pH value back to be suitable for the normal growth of the microalgae. After the treatment, common harmful protozoa in the culturing processes of most microalgae (green algae, blue algae and variegated algae) can be controlled effectively, and the method is also effective on certain miscellaneous algae contamination.

14 Claims, 11 Drawing Sheets

METHOD FOR EFFECTIVELY CONTROLLING HARMFUL ORGANISMS IN LARGE-SCALE CULTURE OF MICROALGAE

The present application is the US National Phase entry under §371 and claims the benefit of International Application No. PCT/CN2010/001135, filed Jul. 26, 2010, which claims the benefit of Chinese Patent Application No. 200910089608.5, filed Jul. 24, 2009, which are incorporated by reference for all purposes.

FIELD OF THE ART

The invention relates to the field of controlling harmful organisms, particularly to a method for effectively controlling harmful organisms in large-scale culture of microalgae.

BACKGROUND OF THE INVENTION

Microalgae have become a remarkable novel industry of energy sources and nutrition. Since systematic sterilization is impossible in large-scale culture of microalgae, contamination is easily caused by harmful organisms. And such contamination usually results in a completely failure of the entire culture. The key of the invention is to provide a convenient and effective method for killing harmful organisms.

1. During the culture of algae, contamination caused by harmful organisms such as protozoa and other algae etc. commonly occurs. The harm caused by harmful organisms to the culture of microalgae is very severe, which often results in a complete failure of culture. The contamination and harm caused by harmful organisms is one of the major reasons that cause unstable quality of microalgae culture currently. And its controlling issue has not been solved till now.

2. Organism-Caused Harm to Culture of Microalgae 1) preying: harmful organisms such as Rotifera, *Oxyrrhis* sp, *Amoeba* sp, and etc. swallow algal cells directly. If the number of harmful organisms and their swallow amount are not large, their impact is not significant due to the fast reproduction rate of algal cells. However, when the number of harmful organisms and their swallow amount are increased, their harm to the culture of microalgae will become severe. In particular, Rotifera has a huge swallow amount. Algal cells can be eaten completely within 2-3 days, thereby resulting a clear algal liquid.

2) inhibiting and poisoning microalgae by secreting harmful substances: harmful organisms inhibit and poison algal cells by secreting certain harmful extracellular products, which is another aspect of the harm caused by harmful organisms and normally severer than direct swallowing. When harmful organisms secret a small amount of harmful substances, the cultured algae grow slowly. When harmful organisms reproduce in a large number and secret more harmful substances, a great deal of algal cells sink and die. The harmful substances secreted by harmful organisms have different toxic levels to different types of algae. The harm caused by a harmful organism maybe involves any one aspect or both aspects described above.

3. Strategies for Controlling Harmful Organisms

The principle of treating the contamination and harm caused by harmful organisms is mainly based on prevention or combination of prevention and control, i.e. reduction of their harmful level as low as possible.

1) Preventing Strategies (1) In the process of culture, each production part is sterilized strictly and the environment is kept as sterile as possible, so as to prevent contamination from the initial source.

(2) Separating, culturing and supplying algae: in the process of culture, strict prevention of contamination is very important. However, from the point of view of the current technical level of microalgae culture, the contamination caused by harmful organisms is impossible to be prevented completely during a long-term cultivation. As a result, contamination occurs sooner or later, and harmful organisms can reproduce dramatically in a suitable condition and eventually result in the failure of culture. In order to solve this problem radically, the algae that have been contaminated during the long-term cultivation should be replaced by fresh pure algae constantly, which may enable the culture to go on wheels. Therefore, separation, culture and supply of algae are very important.

(3) Maintaining the growth and number dominance of the cultured algae: good growth of the cultured algae and their absolute number dominance in alga liquid are very important for preventing and alleviating the harm caused by harmful organisms. It has been taught by the experience in long-term cultivation that when the cultured algae grow well and reproduce rapidly, severe harm caused by harmful organisms occurs less frequently. Sometimes although the algae have been contaminated, harmful organisms is not increased, but decreased or even disappear after a period of cultivation. Therefore, maintenance of good growth of the cultured algae and their number dominance and inhibition of harmful organisms by secreting more extracellular product is one of the reasons that lead to success of culturing. To maintain algae to grow well, first, the inoculated algae must be obtained in the exponential growth phase and second, the environmental condition should satisfy the requirement for alga growth as close as possible and allow the algae to grow prosperously. The algae should be inoculated in a large amount. As a result, the algae have an absolute number dominance in the culture liquid from the beginning of cultivation.

2) Methods for eliminating, inhibiting or killing harmful organisms

The following three methods are usually used for eliminating, inhibiting or killing harmful organisms.

(1) Eliminating Large-Sized Harmful Organisms by Filtering

The large-sized contaminating harmful organisms (e.g. Rotifera, etc.) can be eliminated by filtering, because all bait algae are small. Typically, Rotifera can be filtered through a screening silk with meshes less than 60 um. After filtered once, adult Rotifera can be eliminated, but the eggs and the younger individuals under developing cannot been eliminated completely until completion of 3-daycontinuous filtering, once a day. When the eggs and younger individuals remained after the first round of filtering develop into adults, they can be eliminated in the second or third round of filtering.

(2) Inhibiting or Killing Harmful Organisms with Drugs

The drugs for inhibiting or killing harmful organisms are used.

(3) Killing Harmful Organisms by Changing Environmental Conditions

In order to use the method for killing harmful organisms by changing environmental conditions, ranges of the environmental factors such as temperature, salinity, pH etc. suitable for culturing algae and harmful organisms must be understood. Then according to a specific situation, a certain environmental factor can be altered to achieve the purpose of killing harmful organisms but preserving algae.

DISCLOSURE OF THE INVENTION (1) Technical Problem to be Solved

The contamination caused by harmful organisms is unavoidable in the process of culturing microalgae. Sometimes such contamination may result in the failure of the entire culture because it cannot be controlled.

Currently, controlling of microalgae contamination mainly focuses on prevention. Sterilization of culturing system is difficult to be achieved for large-scale culture, and leads to a higher cost. In order to maintain the dominance in population, purification of the algae should be carried out and a larger inoculation amount should be maintained, which will also raise the cost in large-scale culture. For keeping a high sterile level and a large amount, a high requirement for techniques and devices needs to be fulfilled, and all parts of the entire running process should be maintained as sterile all the time, which also raises the running cost and becomes the bottleneck of large-scale production.

Contamination caused by large-sized organisms is mainly treated by filtering; whereas contamination caused by small-sized organisms is mainly treated with drugs. However, filtering raises the running cost for large scale production, and the drugs kill both protozoa and algae which makes the algae unable to resume growth shortly and even die in a large amount. Moreover, the in-time collecting method is also used right after contamination.

(2) Technical Protocol

The entire invention is shown as FIG. 1. Different pH treatment protocol is selected according to the tolerance of contaminated organisms. Based on the species and degree of contamination, both treatments may be combined, and finally the samples are adjusted to the pH suitable for alga growth by aerated with air or $CO_2$ and cultured in such an environment continuously.

The feature of the invention is to effectively control the contamination caused by harmful organisms by adjusting pH value. Most organisms cannot survive in an environment of saturated carbon dioxide and higher pH. However, many algae have stronger tolerance and can resume activity more quickly in a suitable environment.

1. The pH tolerance of the contaminating species is determined by experience or a preliminary experiment in the contaminated culture system, then the system is treated in an intolerable pH environment.

2. In the case of more harmful organism species and severer contamination, different pH treatment is carried out according to the severity level of the contaminated species. When the contaminated species is observed to be in control under a microscope, pH is adjusted to a pH suitable for microalgae growth. For most algae, growth can be resumed in 24 hours.

3. The used treatment is simple, convenient, low cost, and has no impact on later-stage products. The treatment after adjustment is also very simple. Some methods such as sufficient aerating air and appropriate temperature rising, etc. can be used to rapidly resume the pH value to the range required for optimal growth status. Some basic substances such as NaOH, ammonia and the like can also be used if necessary.

Herein, the following terms are defined specifically:

Harmful organisms: other organisms that compete with or prey on the cultured algae in the culture of microalgae.

Effectively killing or inhibiting harmful organisms: the microscopic examination of such harmful organism shows significant reduction of number, imperfection of cell morphology or loss of activity.

Optimal pH value for microalgae growth: the optimal pH environment for microalgae growth, which varies for different species, usually in a range of 7.0-9.0.

Harmful organisms with acid or alkali tolerance: a pH gradient experiment is performed on contaminated alga liquid, and its acid or alkali tolerance is determined under a microscope, wherein normally, the harmful organisms with alkali tolerance refer to the organisms that possess strong tolerance against a high pH environment and can survive in a high pH environment; the harmful organisms with acid tolerance refer to the organisms that can survive in a lower pH environment.

Mixed harmful organisms: the contaminating species is not a single contamination, and different contamination has different tolerance.

pH tolerance limit of algae: the lowest and highest limits of pH value that can be tolerated by algae.

The detailed embodiments of the invention are described below by referring to FIG. 1:

The invention provides a method for effectively controlling harmful organisms in large-scale culture of microalgae, said method includes the following steps:

a. determining the harmful organism species causing contamination to the algae, and the acid and alkali tolerance levels of said harmful organism species;

b. adjusting the pH value of the microalgae culture system according to the different acid and alkali tolerance levels of the harmful organisms, and then adjusting the pH value back to the optimal pH for the growth of said microalgae when the harmful organisms are killed or inhibited effectively.

As shown in FIG. 1, the types of the contamination to the contaminated algae liquid is firstly determined. Usually, the contamination to the contaminated alga liquid is divided into 3 types: alkali tolerant contamination, acid tolerant contamination, and mixed contamination. Among others, the harmful organisms causing alkali tolerant contamination mainly include the contaminating species that have strong tolerance against high pH value, such as *Amoeba* sp. The harmful organisms causing acid tolerant contamination mainly include the contaminating species that have strong tolerance against low pH value, such as *Oxyrrhis* sp. The harmful organisms causing mixed contamination mainly include plural contaminating species, for example, contamination of both *Amoeba* and ciliate. In order to determine the harmful organism species causing contamination, the following procedure can be carried out: the appearance of the species causing contamination of alga liquid is observed under a microscope, and the contaminating species is preliminarily identified through a normal appearance comparison; if the contamination is a uncommon one, then a pH gradient is set up by adjusting pH value of the contaminated alga liquid with acids or alkalis, followed by observation of the appearance of contaminating species and microalgae, so as to determine the optimal treatment protocol.

If the contaminated alga liquid is identified as alkali tolerant contamination, $CO_2$ is aerated into the culture system of microalgae, so as to lower the pH value. At this time, the appearance of the algae cells and the harmful organisms are observed under a microscope. When the harmful organisms has been inhibited or inactivated, air is sufficiently aerated into the culture system and the pH value is adjusted back to the optimal pH suitable for microalgae growth. In an embodiment, the concentration of $CO_2$ reaches saturation. In an alternative embodiment, the pH value can be adjusted back to the optimal pH suitable for microalgae growth with ammonia (one of the nitrogen sources used by microalgae). In an embodiment, the pH value can be adjusted back to the optimal pH suitable for microalgae growth with NaOH. In an embodiment, the used NaOH is 1M NaOH. In an embodiment, the pH is 5.6-5.7 in the alga culture system with a saturated concentration of $CO_2$. In an alternative embodiment, if the algae are marine algae (such as in the case of *Dunaliella tertiolecta*), the aerated $CO_2$ can maintain pH within the range of 6.0-6.5. After that, if the harmful organisms have been determined to be in control (for instance, most of Amoeba have become spherical), salinity is reduced by diluting with water (salinity is the ratio between the mass of the solute in seawater and the mass of seawater), followed by sufficient aeration with air, so as to adjust the pH and salinity to a condition suitable for alga growth. In an embodiment (for example, in the case that the alga is *Nannochloris* sp. or *Dunaliella tertiolecta*), $CO_2$ can be aerated intermittently. In an embodiment, $CO_2$ can be aerated at an interval of two hours. In an embodiment, the culture system is maintained at pH 6.0-6.5 for 2 days, followed by decreasing 1% of the salinity by adding water. In an embodiment, the culture system is maintained with saturated $CO_2$ for about 28 hours. In an embodiment, $CO_2$ is kept at saturation for about 27 hours in the culture system. In an embodiment, saturated $CO_2$ is aerated continuously into the culture system for 36 hours. In an embodiment, $CO_2$ is aerated periodically at an interval of 2 hours (pH is in the range of 5.0-8.5), for 2 days.

If the contaminated alga liquid is identified as acid tolerant contamination, pH value is raised up with alkalis in the culture system of the microalgae and maintained for a period of time. The pH value cannot be higher than the maximal tolerable pH of the microalgae. When the harmful organisms are observed as being inactivated or lysed under a microscope (for example, no *Oxyrrhis* that is integrated and moves fast can be observed under a microscope), the pH value is then adjusted back to suit microalgae growth. In an embodiment, said alkali can be ammonia. In an embodiment, said alkali can be NaOH. In an embodiment, said alkali can be 1M NaOH. Depending on different pH requirements and different culture systems, alkalis with different concentrations can be used according to the agitation condition, as long as the transient pH is not too high to be harmful to microalgae, and dilution of the cell concentration in the culture system (caused by adding too much alkali solution) should also be avoided. In an embodiment, said alkali can be other types of alkalis that do not result in any harm caused by accumulation in microalgae, such as ammonia, NaOH, KOH and other soluble alkalis. In an embodiment, the pH of the culture system is adjusted to 11.5-12.0 with 1M NaOH or 1M ammonia. In an embodiment, the pH of the culture system is adjusted to 11.0-11.8 or 8.0-11.0 with 1M NaOH or 1M ammonia. In an embodiment, the pH of the culture system is adjusted to 8.0-11.0, 11.5-12.0 or 11.0-11.8 and maintained for 3 hours.

If the contaminated alga liquid is identified as mixed contamination, for example, the harmful organism-caused contamination including both acid tolerant contamination and alkali tolerant contamination, the following treatment is carried out depending on the species, harming rate and degree, as well as acid/alkali tolerance of the harmful organisms:

(1) In the case that alkali tolerant contamination is relatively severe, the sample is firstly treated at a low pH for a while; after a greater inhibiting and killing impact of this treatment is determined on the targeted harmful organisms, the harmful organisms with the opposite tolerance are treated at a high pH; the pH value is adjusted back to be suitable for the normal growth of the microalgae when the harmful organisms are determined to be killed or inhibited effectively; or (2) In the case that acid tolerant contamination is relatively severe, the sample is firstly treated at a high pH for a while; after a greater inhibiting and killing impact of this treatment is determined on the targeted harmful organisms, the harmful organisms with the opposite tolerance are treated at a low pH; the pH value is adjusted back to be suitable for the normal growth of the microalgae when the harmful organisms are determined to be killed or inhibited effectively.

In an embodiment, adjustment of pH back to the pH suitable for the normal growth of the algae is performed by sufficiently aerating air, or adjustment of pH back to the pH suitable for the normal growth of the algae from a higher pH is accomplished by aerating $CO_2$, and real-time checking pH value.

In an embodiment, the pH of the culture system is first raised by alkalis, followed by aeration of $CO_2$ to saturation. When the harmful organisms are observed as being in control under a microscope (for example, these harmful organisms such as *Oxyrrhis, Amoeba* and ciliate cannot be observed under a microscope or the activity of the harmful organisms has been reduced), the pH value is then adjusted back to the optimal pH suitable for microalgae growth by sufficiently aerating air. In an embodiment, an interval of 1 hour exists between the step of raising pH of the culture system with an alkali and the step of aerating $CO_2$ to saturation. In an embodiment, said alkali can be ammonia. In an embodiment, said alkali can be 1M NaOH. In an embodiment, said alkali can be other types of alkalis that do not result in any harm caused by accumulation in microalgae, such as ammonia, NaOH, KOH and other soluble alkalis. In an embodiment, the pH of the culture system is adjusted to 11.5-12.0, 11.0-11.8 or 8.0-11.0 with 1M NaOH or 1M ammonia. In an embodiment, the pH of the culture system is adjusted to 11.5-12.0, 11.0-11.8 or 8.0-11.0 and maintained for 1 hours, followed by aeration of $CO_2$ to saturation for about 24 hours. In an embodiment, the pH of the culture system is adjusted to 11.5-12.0, 11.0-11.8 or 8.0-11.0 and maintained for 1 hours, followed by aeration of $CO_2$ to saturation for about 23 hours.

Using the above method, the harmful organisms causing alga contamination are in control. During the period after the pH returns back to the normal pH, the cultured algae start to grow normally.

In the embodiments described above, the used microscope generally is Nikon fluorescent invert microscope Ti series.

(3) Effect of the Invention

All common harmful protozoa in the culturing processes of most microalgae (green algae, blue algae and variegated algae) can be controlled effectively, and the invention is also effective on certain miscellaneous algae contamination.

(4) Novelty and Inventiveness of the Invention

1. The method of the invention has the advantages of low cost, convenience and higher feasibility, and dramatically reduces the impact of contamination on production and the cost for treating contamination. So it is first choice to treat contamination in large-scale culturing process.

2. The pH can be easily adjusted back to be suitable for algae growth after the treatment of the method, which results in less impact on growth rate of algae and no impact on culturing period and yield.

3. Variety of environmental factors, such as salinity, temperature, etc. can be used in combination with pH, so as to improve the rate and result of controlling.

Particularly, compared with prior art, the invention has the following major distinctive features:

(1) the invention relates to the harmful organism species causing contamination to the microalgae in culture; and the appropriate treatment depending on the acid and alkali tolerance levels of said harmful organism species;

(2) the inventive technique for preventing and treating harmful organisms by adjusting pH does not affect the bioactivity of microalgae (most microalgae lose activity at a pH of 4 or lower; and have even lower activity at a pH of 1 or lower);

(3) the pH adjustment in the invention is conducted by adding $CO_2$, nitrogen source and the like which does not impair the activity of microalgae but benefits the growth of microalgae, rather than by adding chemicals;

(4) the invention involves not only the step of adjusting pH value, but also the step of killing harmful organisms by transiently adjusting both salinity and pH; and after the harmful organisms have been killed, the salinity is recovered, which results in no impact on the growth of microalgae;

(5) the technique of the invention is used for both controlling and preventing/treating harmful organisms; using the inventive method, harmful organisms can be killed at the early stage by periodically adjusting pH and salinity without addition of any high-cost chemical that is disadvantageous to growth when the harmful organisms are not spread out.

DESCRIPTION OF THE FIGURES

FIG. 2 shows the low pH treatment of *Amoeba* contamination in *Dunaliella tertiolecta*. After the cultivation of about 144 h, *Amoeba* contamination was found under a microscope with an oil immersion lens. Then $CO_2$ was aerated intermittently to keep pH within the range of 6.0-6.5 for 2 days. Salinity was decreased by 1% by adding water. The growth of *Dunaliella tertiolecta* was not affected essentially.

FIG. 3 shows that after about the cultivation of 196 h, *Oxyrrhis* contamination was found in the culture of *Chlorella* sp. pH was adjusted to 11.0-11.8 with 1M NaOH. Three hours later, $CO_2$ was sufficiently aerated to adjust pH to 7.0-8.0. *Chlorella* sp. started to grow after about 18 hours.

FIG. 4 shows that the *Amoeba* contamination was found after about culturing *Chlorella* sp. for 72 hours. $CO_2$ was aerated to be saturated in the culture system. About 28 hours later, almost no *Amoeba* was found under a microscope. And *Chlorella* sp. started to grow after about 28 hours.

FIG. 5 shows that the contaminations caused by *Amoeba*, *Oxyrrhis*, and ciliate were found after about culturing *Chlorella* sp. for 72 hours. pH was adjusted to 11.0-11.8 with 1M NaOH for one hour. Then, $CO_2$ was aerated to be saturated for about 24 hours. Then air was sufficiently aerated. *Chlorella* sp. resumed to grow after about 24 hours.

FIG. 6 shows that *Amoeba* contamination was found after culturing *Chlorococcum* sp. for 5 days. $CO_2$ was aerated to be saturated for about 27 hours. Then air was sufficiently aerated. *Chlorococcum* sp. started to grow after 8 hours.

FIG. 7 shows that *Oxyrrhis* contamination was found after culturing *Chlorococcum* sp. for 3 days. pH was adjusted to 11.5-12.0 with 1M NaOH. Three hours later, $CO_2$ was aerated to adjust pH to 7.0-8.0. *Chlorococcum* sp. started to grow after about 18 hours.

FIG. 8 shows that mixed contamination was found after culturing *Chlorococcum* sp. for 4 days. pH was adjusted to 11.5-12.0 with 1M NaOH. One hour later, $CO_2$ was aerated to be saturated for about 24 hours. Then air was sufficiently aerated. *Chlorococcum* sp. started to grow after about 18 hours.

FIG. 9 shows that diatom contamination was found under a microscope on Day 6 in the process of culturing *Chlorococcum* sp. $CO_2$ was aerated continuously for 36 hours. Then air was sufficiently aerated. Diatom grew slowly, whereas *Chlorococcum* sp. grew normally.

FIG. 10 shows that *Amoeba* contamination was found after Day 4 in the whole process of culturing *Nannochloris*. $CO_2$ was aerated periodically at an interval of 2 hours for 2 days. The growth of *Amoeba* was essentially in control, whereas the growth of *Nannochloris* was not affected.

FIG. 11 shows that mixed contamination was found after culturing *Spirulina maxima* for 7 days. pH was adjusted to 11.5-12.0 with 1M NaOH for one hour. $CO_2$ was aerated to be saturated for about 23 hours. Then air was sufficiently aerated. *Spirulina maxima* resumed to grow after 24 hours.

DETAILED EMBODIMENTS OF THE INVENTION

Figure 1:
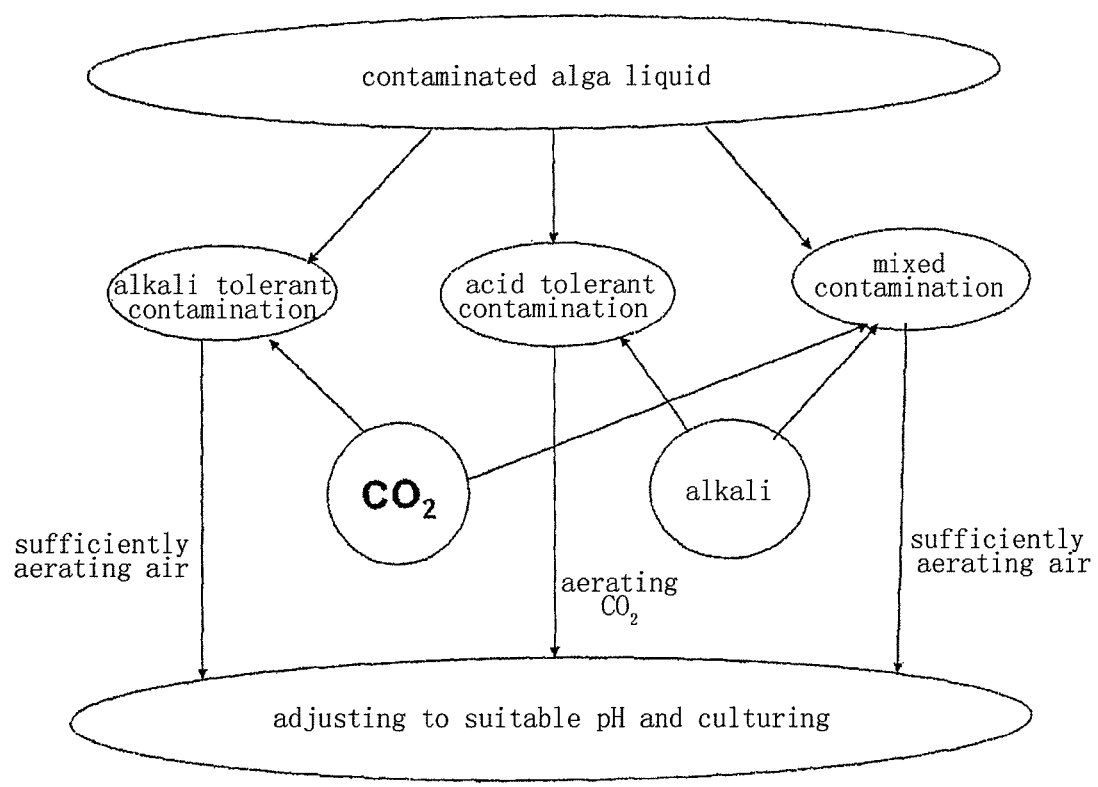
FIG. 1 is a flow chart of the method for effectively controlling harmful organisms in large-scale culture of microalgae.

The invention will be further described in details by incorporating with the Examples. These Examples are only intended to illustrate the invention. The scope of the invention is not limited by these Examples.

EXAMPLES

The general process of the method for effectively controlling harmful organisms in the large-scale culture of microalgae comprises:

1. Determination of Contamination of Microalgae Culture:

Microscope examination is always used as one of the bases for determining the growth status in the process of microalgae culture. As a result, all the early-stage contamination is found by microscope examination. For example, when the alga liquid without microscope examination is contaminated, it's color generally changes into e.g. brown or brown spots are observed on the wall of the reactor, etc. However the contamination has become severer once the color change is observed directly. Therefore, constant microscope examination is suggested to be performed during the culture period, which results in better effect in early-stage controlling.

2. Determination of Contamination Types:

After contamination is found by microscope examination, the contaminating species is determined by normal morphological comparison. If the contaminating species is unknown, a pH gradient experiment is performed to the alga liquid to identify its acid and alkali tolerance.

3. Identification of pH Tolerant Limit of Algae:

pH of the normally cultured microalgae is adjusted into various ranges. The growth rate of the microalgae is measured and their appearance is observed under a microscope.

Formulation of the Culture Medium Used in Examples:

TABLE 1

Formulation of Erdschreiber's Medium

| # | Ingredient | Amount |
|---|---|---|
| 1 | Supplemented seawater | 3 L |
| 2 | P-IV metal element | 36 mL/3 L |
| 3 | $NaNO_3$ | 10 mL/3 L |
| 4 | $Na_2HPO_4 \cdot 7H_2O$ | 10 mL/3 L |
| 5 | Soil water | 150 mL/3 L |
| 6 | vitamin B12 | 3 mL/3 L |

Artificial seawater

| | | |
|---|---|---|
| 1 | NaCl | 49.726 g/L |
| 2 | $MgCl_2$ | 7.26 g/L |
| 3 | $MgSO_4$ | 3.248 g/L |
| 4 | $CaCl_2$ | 1.153 g/L |
| 5 | $NaHCO_3$ | 0.198 g/L |
| 6 | KCl | 0.721 g/L |
| 7 | NaBr | 0.058 g/L |
| 8 | $H_3BO_3$ | 0.058 g/L |
| 9 | $Na_2SiO_3$ | 0.0024 g/L |
| 10 | $Na_2Si_4O_9$ | 0.0015 g/L |
| 11 | $H_3PO_4$ | 0.002 g/L |
| 12 | $Al_2Cl_6$ | 0.013 g/L |
| 13 | $NH_3$ | 0.002 g/L |
| 14 | $LiNO_3$ | 0.0013 g/L |
| 15 | $Na_2SO_4$ | 4 g/L |

P-IV metal element

| | | |
|---|---|---|
| 1 | $Na_2EDTA \cdot 2H_2O$ | 0.75 g/L |
| 2 | $FeCl_3 \cdot 6H_2O$ | 0.097 g/L |
| 3 | $MnCl_2 \cdot 4H_2O$ | 0.041 g/L |
| 4 | $ZnCl_2$ | 0.005 g/L |
| 5 | $CoCl_2 \cdot 6H_2O$ | 0.002 g/L |
| 6 | $Na_2MoO_4 \cdot 2H_2O$ | 0.004 g/L |

Soil water

| | | |
|---|---|---|
| 1 | Soil | 15 g/200 mL $dH_2O$ |
| 2 | $CaCO_3$ (optional) | 1 mg/200 mL $dH_2O$ | vitamin B12

| | | |
|---|---|---|
| 1 | HEPES buffer pH 7.8 | 2.4 g/200 mL dH2O |
| 2 | Vitamin B12 (cyanocobalamin, Sigma V2876) | 0.027 g/200 mL dH2O |

TABLE 2

SM medium

| # | Ingredient | Amount |
|---|---|---|
| 1 | Spir 1 | 500 mL/L |
| 2 | Spir 2 | 500 mL/L |

Spir 1

| | | |
|---|---|---|
| 1 | $NaHCO_3$ | 6.81 g/500 mL $dH_2O$ |
| 2 | $Na_2CO_3$ | 4.03 g/500 mL $dH_2O$ |
| 3 | $K_2HPO_4$ | 0.5 g/500 mL $dH_2O$ |

Spir 2

| | | |
|---|---|---|
| 1 | $NaNO_3$ | 2.5 g/500 mL |
| 2 | $K_2SO_4$ | 1 g/500 mL |
| 3 | NaCl | 1 g/500 mL |
| 4 | $MgSO_4 \cdot 7H_2O$ | 0.2 g/500 mL |
| 5 | $CaCl_2 \cdot 2H_2O$ | 0.04 g/500 mL |
| 6 | P-IV metal element | 6 mL/0.5 L |

TABLE 2-continued

SM medium

| # | Ingredient | Amount |
|---|---|---|
| 7 | Chu microelements | 1 mL/0.5 L |
| 8 | vitamin $B_{12}$ | 1 mL/0.5 L |

P-IV metal element

| | | |
|---|---|---|
| 1 | $Na_2EDTA \cdot 2H_2O$ | 0.75 g/L |
| 2 | $FeCl_3 \cdot 6H_2O$ | 0.097 g/L |
| 3 | $MnCl_2 \cdot 4H_2O$ | 0.041 g/L |
| 4 | $ZnCl_2$ | 0.005 g/L |
| 5 | $CoCl_2 \cdot 6H_2O$ | 0.002 g/L |
| 6 | $Na_2MoO_4 \cdot 2H_2O$ | 0.004 g/L | chu microelements

| | | |
|---|---|---|
| 1 | $CuSO_4 \cdot 5H_2O$ | 0.02 g/L |
| 2 | $ZnSO_4 \cdot 7H_2O$ | 0.044 g/L |
| 3 | $CoCl_2 \cdot 6H_2O$ | 0.02 g/L |
| 4 | $MnCl_2 \cdot 4H_2O$ | 0.012 g/L |
| 5 | $Na_2MoO_4 \cdot 2H_2O$ | 0.012 g/L |
| 6 | $H_3BO_3$ | 0.62 g/L |
| 7 | $Na_2EDTA \cdot 2H_2O$ | 0.05 g/L | vitamin B12

| | | |
|---|---|---|
| 1 | HEPES buffer pH 7.8 | 2.4 g/200 mL dH2O |
| 2 | Vitamin B12 (cyanocobalamin, Sigma V2876) | 0.027 g/200 mL dH2O |

TABLE 3

Formulation of Modified BG-11 medium

| Name | | Concentration (g/L) |
|---|---|---|
| sodium nitrate | $NaNO_3$ | 0.75 |
| dipotassium hydrogen phosphate | $K_2HPO_4$ | 0.039 |
| magnesium sulfate heptahydrate | $MgSO_4 \cdot 7H_2O$ | 0.075 |
| calcium chloride | $CaCl_2$ | 0.027 |
| citric acid | Citric acid | 0.006 |
| ferric citrate | Fe citrate | 0.006 |
| ethylenediaminetetraacetic acid | EDTA | 0.001 |
| sodium carbonate | $NaCO_3$ | 0.02 |
| sodium silicate nonahydrate | $Na_2SiO_3 \cdot 9H_2O$ | 0.058 |
| microelements | Microelements | 1 Ml |

| Microelements | | Concentration (g/L) |
|---|---|---|
| boric acid | $H_3BO_3$ | 2.86 |
| manganese chloride | $MnCl_2$ | 1.81 |
| zinc sulfate heptahydrate | $ZnSO_4 \cdot 7H_2O$ | 0.222 |
| sodium molybdate dihydrate | $Na_2MoO_4 \cdot 2H_2O$ | 0.391 |
| copper sulfate pentahydrate | $CuSO_4 \cdot 5H_2O$ | 0.079 |
| cobaltous nitrate hexahydrate | $Co(NO_3)_2 \cdot 6H_2O$ | 0.0494 |

TABLE 4

Formulation of Modified BG-11 medium

| Name | | Concentration (g/L) |
|---|---|---|
| sodium nitrate | $NaNO_3$ | 0.75 |
| dipotassium hydrogen phosphate | $K_2HPO_4$ | 0.039 |
| magnesium sulfate heptahydrate | $MgSO_4 \cdot 7H_2O$ | 0.075 |

TABLE 4-continued

Formulation of Modified BG-11 medium

| | | |
|---|---|---|
| calcium chloride | $CaCl_2$ | 0.027 |
| citric acid | Citric acid | 0.006 |
| ferric citrate | Fe citrate | 0.006 |
| ethylenediaminetetraacetic acid | EDTA | 0.001 |
| sodium carbonate | $NaCO_3$ | 0.02 |
| sodium silicate nonahydrate | $Na_2SiO_3 \cdot 9H_2O$ | 0.058 |
| microelements | Microelements | 1 Ml |
| sea salt | | 30 g/L |

| Microelements | | Concentration (g/L) |
|---|---|---|
| boric acid | $H_3BO_3$ | 2.86 |
| manganese chloride | $MnCl_2$ | 1.81 |
| zinc sulfate heptahydrate | $ZnSO_4 \cdot 7H_2O$ | 0.222 |
| sodium molybdate dihydrate | $Na_2MoO_4 \cdot 2H_2O$ | 0.391 |
| copper sulfate pentahydrate | $CuSO_4 \cdot 5H_2O$ | 0.079 |
| cobaltous nitrate hexahydrate | $Co(NO_3)_2 \cdot 6H_2O$ | 0.0494 |

Example 1

Low pH treatment for *Amoeba* Contamination in culture of *Dunaliella tertiolecta*

Figure 2:
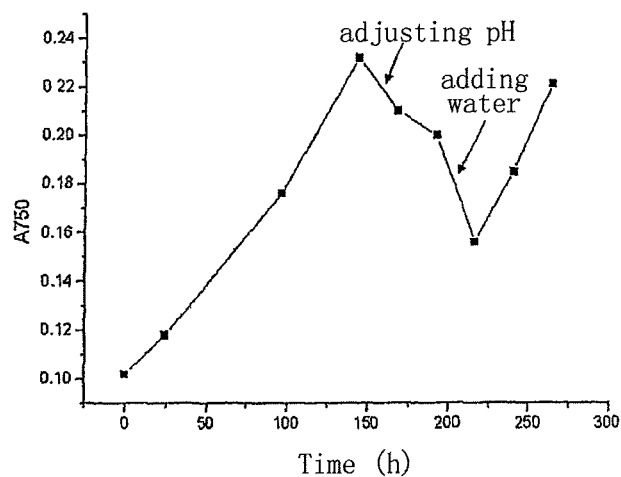
FIG. 2 (Example 1) is a diagram showing the treatment for contamination of *Dunaliella tertiolecta* by a 120 L bubbling reactor.

*Dunaliella tertiolecta* (purchased from UTEX) was cultured in a 120 L bubbling reactor (manufactured by Longfang Jiangchuan plexiglass Co. Ltd., φ300 mm×2 m) out-of-doors under a sunlight film. The modified EM medium (Table 1) was used and the culture condition included: an average temperature of about 25□, a humidity of 60%-80%, and an average illumination of 15000-20000 lux (pH 8.0-9.0 for the normal culture). When *Amoeba* contamination was observed with an oil immersion lens (Nikon fluorescent invert microscope Ti series, 1000 X), $CO_2$ was aerated intermittently to maintain pH6.0-6.5. Two days later, the samples were examined under a microscope and most Amoebae were found to become spherical. Salinity was reduced by 1% (e.g. from 9% to 8%) by way of dilution with water. Then air was sufficiently aerated. Twenty-four hours later, the result of microscope examination showed almost no *Amoeba* and little impact on the growth of algae. The details are shown in FIG. 2.

Example 2

High pH treatment for *Oxyrrhis* Contamination in Culture of *Chlorella* sp.

Figure 3:
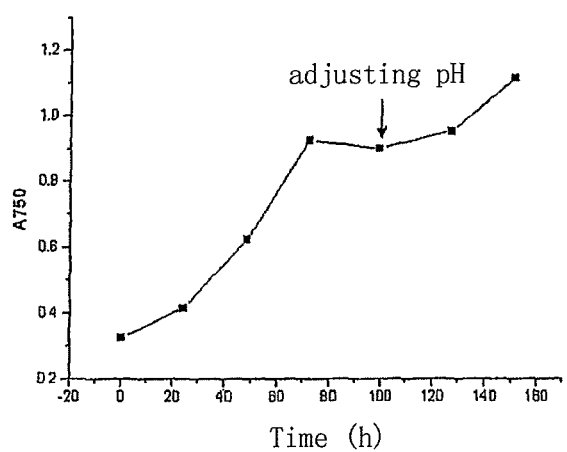
FIG. 3 (Example 2) is a diagram showing the treatment for contamination of to *Chlorella* sp. by a 320 L bubbling reactor.

*Chlorella* sp. (purchased from FACHB collection, Wuhan Aquatic Research Institute, Chinses Academy of Sciences) was cultured in a 320 L bubbling reactor (manufactured by Longfang Jiangchuan plexiglass Co. Ltd., φ300 mm×2 m) out-of-doors under a sunlight film. The culture condition included: a temperature of about 25□, a humidity of 60%-80%, and an illumination of 8000-20000 lux. Modified SM (see Table 2) (pH 7.0-9.0 for the normal culture) was used. When *Oxyrrhis* contamination was observed with an oil immersion lens (Nikon fluorescent invert microscope Ti series), pH was adjusted to 11.0-11.8 with 1M NaOH. Three hours later, the result of microscope examination showed almost no *Oxyrrhis*. Then, $CO_2$ was aerated to adjust pH to be 7.0-8.0. The *Chlorella* sp. started to grow after 18 hours. The details are shown in FIG. 3.

Example 3

Saturated $CO_2$ treatment for *Amoeba* Contamination in Culture of *Chlorella* sp.

Figure 4:
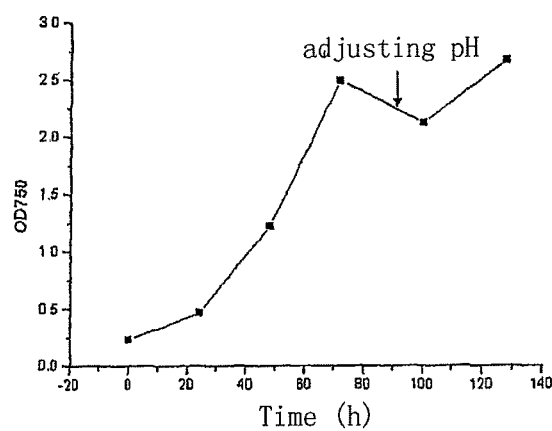
FIG. 4 (Example 3) is a diagram showing the treatment for contamination of *Chlorella* sp. by a 320 L bubbling reactor.

*Chlorella* sp. (purchased from FACHB collection, Wuhan Aquatic Research Institute, Chinses Academy of Sciences) was cultured in a 320 L bubbling reactor (manufactured by Longfang Jiangchuan plexiglass Co. Ltd., φ300 mm×2 m) out-of-doors under a sunlight film. Modified SM medium (see Table 2) (pH 7.0-9.0 for the normal culture) was used. The culture condition included: a temperature of about 25□, a humidity of 60%-80%, and an illumination of 8000-20000 lux. When *Amoeba* contamination was observed with an oil immersion lens (Nikon fluorescent invert microscope Ti series), $CO_2$ was aerated continuously (pH value is about 5.6-5.7 when $CO_2$ is saturated). One hour later, the microscope examination showed that most Amoebae were found to become spherical and lose activity (these Amoebae can not swim and become spherical under microscope). $CO_2$ was aerated continuously and twenty-seven hours later, almost no intact *Amoeba* was observed. Then air was sufficiently aerated, and pH was raised to 7.0-7.5 after 4 hours. Growth of the algae was almost not affected. *Chlorella* sp. started to grow in 24 hours after recovery of pH7.0 or above. The details are shown in FIG. 4.

Example 4

Various pH Treatments for Contamination Caused by Different Species in the Culture of *Chlorella* sp.

Figure 5:
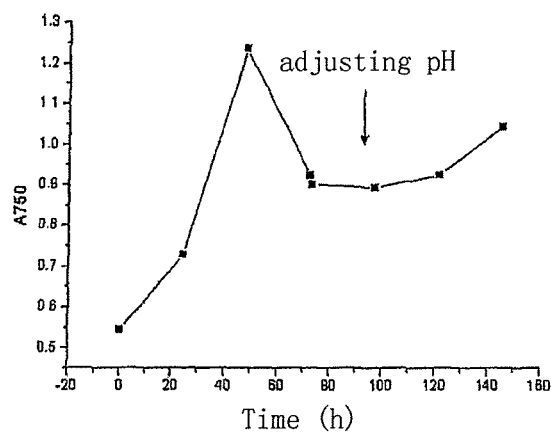
FIG. 5 (Example 4) is a diagram showing the treatment for contamination of *Chlorella* sp. by a 320 L bubbling reactor.

*Chlorella* sp. (obtained from Jinan University) was cultured in a 320 L bubbling reactor (manufactured by Longfang Jiangchuan plexiglass Co. Ltd., φ300 mm×2 m) out-of-doors under a sunlight film (with a temperature of about 25□, a humidity of 60%-80%, and an illumination of 8000-20000 lux). Modified SM medium (see Table 2) was used. When *Amoeba*, *Oxyrrhis* and ciliate contaminations were observed is with an oil immersion lens (Nikon fluorescent invert microscope Ti series), pH was adjusted to 11.0-11.8 with 1M NaOH. One hour later, the result of microscope examination showed that *Oxyrrhis* were essentially inactivated. Then, $CO_2$ was aerated continuously to saturation (pH 5.6). Twenty-four hours later, the alga liquid turned from brown (before the treatment) to green, and the result of microscope examination showed no *Amoeba* or *Oxyrrhis*, but a few inactive and immotile ciliates. Then air was sufficiently aerated. Twenty-four hours later, *Chlorella* sp. could resume to grow. The details are shown in FIG. 5.

Example 5

Saturated $CO_2$ Treatment for *Amoeba* Contamination in Culture of *Chlorococcum* sp.

Figure 6:
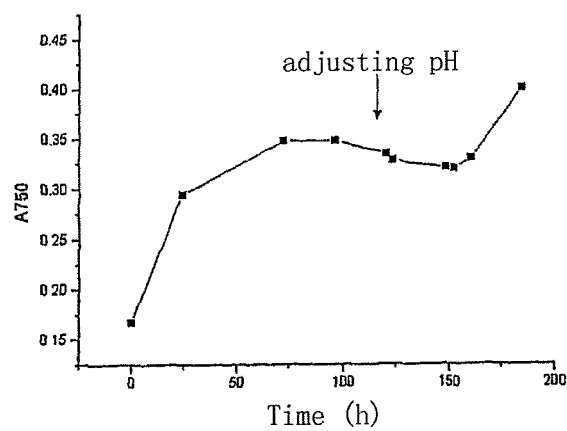
FIG. 6 (Example 5) is a diagram showing the treatment for contamination of *Chlorococcum* sp. by a 60 L glass plate reactor.

*Chlorococcum* sp. (obtained from Qingdao Marine Institute) was cultured (pH 8.0-9.0 for the normal culture) in a 60 L glass plate reactor (manufactured by Longfang Jiangchuan plexiglass Co. Ltd., OP=10 cm) under a sunlight film (with a temperature of about 25□, a humidity of 60%-80%, and an illumination of 8000-20000 lux). Modified BG11 medium (see Table 3) was used. *Amoeba* contamination was observed under an microscope (Nikon fluorescent invert microscope Ti series) on ~Day 5. $CO_2$ was aerated continuously to be saturated in the culture system, and pH was in the range of about 5.6-5.7. One hour later, the result of microscope examination showed that most *Amoeba* turned into spherical, were inactivated and could not change shape or move. $CO_2$ was aerated continuously. Twenty-seven hours later, almost no intact *Amoeba* were observed. Then air was sufficiently aerated, and pH was raised to 7.0-8.0 in 4 hours. Growth of the algae was rarely affected. *Chlorella* sp. started to grow in 8 hours after recovery of pH7.0 or above. The details are shown in FIG. 6.

Example 6

High pH Treatment for *Oxyrrhis* Contamination in Culture of *Chlorococcum* sp.

Figure 7:
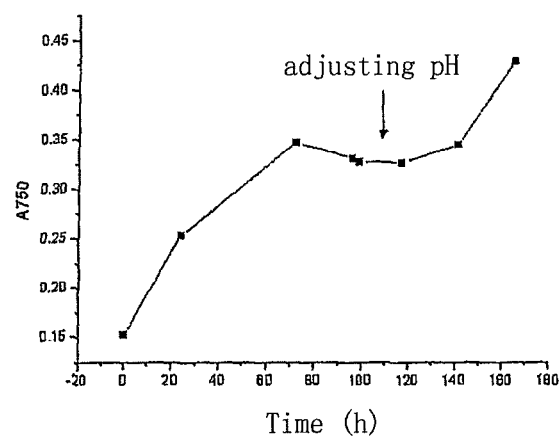
FIG. 7 (Example 6) is a diagram showing the treatment for contamination of *Chlorococcum* sp. by a 60 L glass plate reactor.

*Chlorococcum* sp. (obtained from Qingdao Marine Institute) was cultured in a 60 L glass plate reactor (manufactured by Longfang Jiangchuan plexiglass Co. Ltd., OP=10 cm) under a sunlight film (with a temperature of about 25☐, a humidity of 60%-80%, and an illumination of 8000-20000 lux) (pH 8.0-9.0 for the normal culture). Modified BG11 medium (see Table 3) was used. *Oxyrrhis* contamination was found by microscope examination (Nikon fluorescent invert microscope Ti series) after 3-day cultivation. pH was adjusted to 11.5-12.0 with 1M NaOH. Three hours later, the result of microscope examination showed almost no *Oxyrrhis*. Then $CO_2$ was aerated and pH was adjusted to 7.0-8.0. *Chlorococcum* sp. started to grow in 18 hours. The details are shown in FIG. 7.

Example 7

Various pH Treatments for Contamination Caused by Different Species in the Culture of *Chlorococcum* sp.

Figure 8:
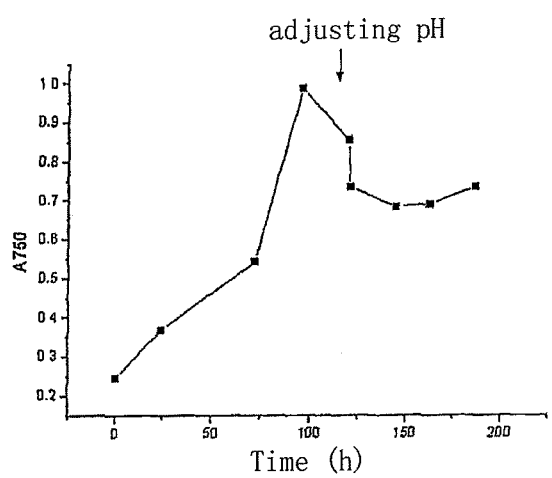
FIG. 8 (Example 7) is a diagram showing the treatment for contamination of *Chlorococcum* sp. by a 60 L glass plate reactor.

*Chlorococcum* sp. (obtained from Qingdao Marine Institute) was cultured in a 60 L glass plate reactor (manufactured by Longfang Jiangchuan plexiglass Co. Ltd., OP=10 cm) under a sunlight film (with a temperature of about 25☐, a humidity of 60%-80%, and an illumination of 8000-20000 lux) (pH 8.0-9.0 for the normal culture). Modified BG11 medium (see Table 3) was used. *Amoeba, Oxyrrhis* and ciliate contaminations were found by microscope examination (Nikon fluorescent invert microscope Ti series) after 4-day cultivation. pH was adjusted to 11.5-12.0 with 1M NaOH. The result of microscope examination showed that *Oxyrrhis* were essentially inactivated. One hour later, $CO_2$ was aerated to saturation (about pH 5.6) for 24 hour continuously. The alga liquid turned from brown (before the treatment) to green, and the result of microscope examination showed no *Amoeba* or *Oxyrrhis*, but a few inactive and immotile ciliates. Then air was sufficiently aerated. Eighteen hours later, *Chlorococcum* sp. could resume to grow. The details are shown in FIG. 8.

Example 8

Control of Diatom Contamination in the Culture of *Chlorococcum* sp.

Figure 9:
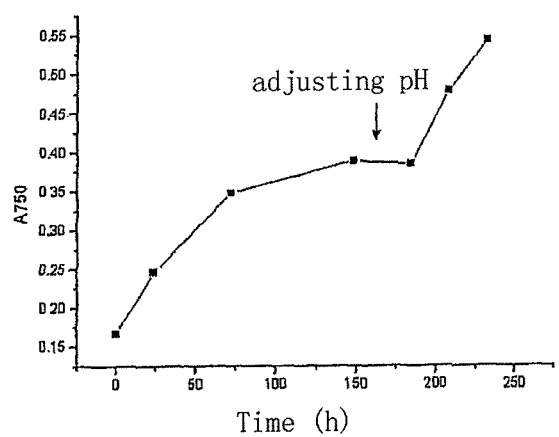
FIG. 9 (Example 8) is a diagram showing the treatment for contamination of *Chlorococcum* sp. by a 60 L glass plate reactor.

*Chlorococcum* sp. (obtained from Qingdao Marine Institute) was cultured in a 60 L glass plate reactor (manufactured by Longfang Jiangchuan plexiglass Co. Ltd., OP=10 cm) under a sunlight film (with a temperature of about 25☐, a humidity of 60%-80%, and an illumination of 8000-20000 lux) (pH 8.0-9.0 for the normal culture). Modified BG11 medium (see Table 3) was used. Diatom contamination was found with an oil immersion lens (Nikon fluorescent invert microscope Ti series). $CO_2$ was aerated continuously to be saturated (about pH 5.6 for now). Thirty-six hours later, the result of microscope examination showed that some diatom lost intracellular pigment and only empty shells were left. Then air was sufficiently aerated. The residual contaminating diatom had reduced activity, grew slowly, and would not become dominant algae. As a result, the contamination level could be effectively controlled and the entire culture of *Chlorococcum* sp. would not be affected. The details are shown in FIG. 9.

Example 9

Low pH Treatment for *Amoeba* Contamination in Culture of *Nannochloris*

Figure 10:
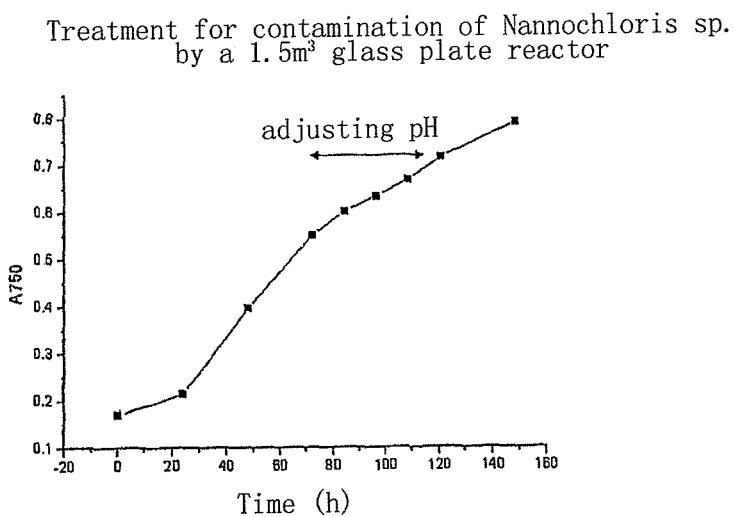
FIG. 10 (Example 9) is a diagram showing the treatment for contamination of *Nannochloris* by a 1.5 $m^3$ glass plate reactor.

*Nannochloris* sp. (obtained from Qingdao Marine Institute) was cultured in a 1.5 $m^3$ glass plate reactor (manufactured by Longfang Jiangchuan plexiglass Co. Ltd., OP=10 cm) under a sunlight film (with a temperature of about 25☐, a humidity of 60%-80%, and an illumination of 8000-20000 lux) (pH 7.0-9.0 for the normal culture). Modified BG11 medium (see Table 4) was used. *Amoeba* contamination was observed with an oil immersion lens (Nikon fluorescent invert microscope Ti series). Then $CO_2$ was aerated periodically at an interval of 2 hours (pH ranged within 5.0-8.5). Two days later, the result of microscope examination showed that no *Amoeba* was observed and the growth rate of the algae was rarely affected. The details are shown in FIG. 10.

Example 10

Control of Contamination of *Spirulina maxima* by Adjusting pH Value

Figure 11:
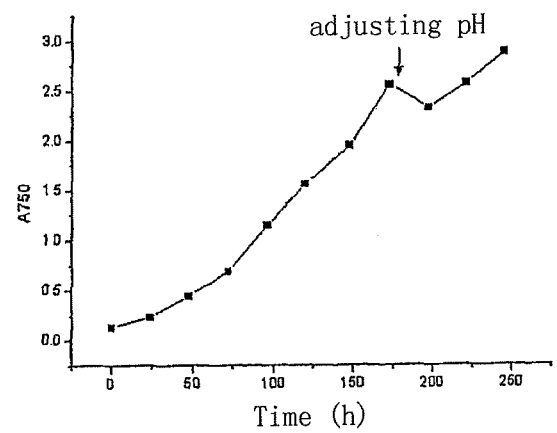
FIG. 11 (Example 10) is a diagram showing the treatment for contamination of by a 500 L raceway pond.

*Spirulina maxima* (purchased from UTEX) was cultured in a 500 L raceway pond (manufactured by Longfang Jiangchuan plexiglass Co. Ltd., φ300 mm×2 m) out-of-doors under a sunlight film (with a temperature of about 25☐, a humidity of 60%-80%, and an illumination of 8000-20000 lux). Modified SM (see Table 2) was used. *Amoeba, Oxyrrhis* and ciliate contaminations were observed by microscope examination (Nikon fluorescent invert microscope Ti series). pH was adjusted to 11.5-12.0 with 1M NaOH. One hour later, $CO_2$ was aerated to saturation (about pH 5.8) for 23 hour continuously. The result of microscope examination showed no *Amoeba* or *Oxyrrhis*, but a few inactive and immotile ciliates. Then air was sufficiently aerated. Twenty-four hours later, the algae could resume to grow. The details are shown in FIG. 11.

Example 11

High pH Treatment for *Oxyrrhis* Contamination in the Culture of *Chlorella* sp.

*Chlorella* sp. (purchased from FACHB collection, Wuhan Aquatic Research Institute, Chinses Academy of Sciences) was cultured in a 320 L bubbling reactor (manufactured by Longfang Jiangchuan plexiglass Co. Ltd., φ300 mm×2 m) out-of-doors under a sunlight film. Modified SM medium (see Table 2) (pH 7.0-9.0 for the normal culture) was used. The culture condition included: a temperature of about 25☐, a humidity of 60%-80%, and an illumination of 8000-20000 lux. When *Oxyrrhis* contamination was observed with an oil immersion lens (Nikon fluorescent invert microscope Ti series), pH was adjusted to 8.0 with 1M ammonia. Three hours later, almost no *Oxyrrhis* was observed by microscope examination. Then $CO_2$ was aerated and pH was adjusted to 7.0-8.0. *Chlorella* sp. started to grow in 18 hours. Compared with the situation of adjusting pH with NaOH, *Chlorella* clearly grew better in this case, because ammonia could be used as the nitrogen source for microalgae growth.

Example 12

Various pH Treatments for Contamination Caused by Different Species in the Culture of *Chlorella*

*Chlorella* sp. (obtained from Jinan University) was cultured in a 320 L bubbling reactor (manufactured by Longfang Jiangchuan plexiglass Co. Ltd., φ300 mm×2 m) out-of-doors under a sunlight film (with a temperature of about 25□, a humidity of 60%-80%, and an illumination of 8000-20000 lux). Modified SM medium (see Table 2) was used. *Amoeba, Oxyrrhis* and ciliate contaminations were observed with an oil immersion lens (Nikon fluorescent invert microscope Ti series). pH was adjusted to 9.0 with 1M ammonia. One hour later, the result of microscope examination showed that *Oxyrrhis* lost its activity essentially. Then $CO_2$ was aerated to saturation (pH 5.6) for 24 hours continuously. The alga liquid turned from brown (before the treatment) to green, and the result of microscope examination showed no *Amoeba* or *Oxyrrhis*, but a few inactive and immotile ciliates. Then air was sufficiently aerated. Twenty-four hours later, *Chlorella* sp. could resume to grow. Compared with the situation of adjusting pH with NaOH, *Chlorella* sp. clearly grew better in this case, because ammonia could be used as the nitrogen source for microalgae growth.

Example 13

High pH Treatment for *Oxyrrhis* Contamination in the Culture of *Chlorococcum* sp.

*Chlorococcum* sp. (obtained from Qingdao Marine Institute) was cultured in a 60 L glass plate reactor (manufactured by Longfang Jiangchuan plexiglass Co. Ltd., OP=10 cm) under a sunlight film (with a temperature of about 25□, a humidity of 60%-80%, and an illumination of 8000-20000 lux) (pH 8.0-9.0 for the normal culture). Modified BG11 medium (see Table 3) was used. *Oxyrrhis* contamination was found by microscope examination (Nikon fluorescent invert microscope Ti series) after 3-day cultivation. pH was adjusted to 10.0 with 1M ammonia. Three hours later, the result of microscope examination showed almost no *Oxyrrhis*. Then $CO_2$ was aerated and pH was adjusted to 7.0-8.0. *Chlorococcum* sp. started to grow in 18 hours. Compared with the situation of adjusting pH with NaOH, *Chlorococcum* sp. clearly grew better in this case, because ammonia could be used as the nitrogen source for microalgae growth.

Example 14

Various pH Treatments for Contamination Caused by Different Species in the Culture of *Chlorococcum* sp.

*Chlorococcum* sp. (obtained from Qingdao Marine Institute) was cultured in a 60 L glass plate reactor (manufactured by Longfang Jiangchuan plexiglass Co. Ltd., OP=10 cm) under a sunlight film (with a temperature of about 25□, a humidity of 60%-80%, and an illumination of 8000-20000 lux) (pH 8.0-9.0 for the normal culture). Modified BG11 medium (see Table 3) was used. *Amoeba, Oxyrrhis* and ciliate contaminations were observed by microscope examination (Nikon fluorescent invert microscope Ti series) after 4-day cultivation. pH was adjusted to 9.0 with 1M ammonia. The result of microscope examination showed that *Oxyrrhis* was inactivated essentially.

One hour later, $CO_2$ was aerated to saturation (about pH 5.6) for 24 hour continuously. The alga liquid turned from brown (before the treatment) to green, and the result of microscope examination showed no *Amoeba* or *Oxyrrhis*, but a few inactive and immotile ciliates. Then air was sufficiently aerated. Eighteen hours later, *Chlorococcum* sp. could resume to grow. Compared with the situation of adjusting pH with NaOH, *Chlorococcum* sp. clearly grew better in this case, because ammonia could be used as the nitrogen source for microalgae growth.

Example 15

Control of Contamination of *Spirulina maxima* by Adjusting pH Value

*Spirulina maxima* (purchased from UTEX) was cultured in a 500 L raceway pond (manufactured by Longfang Jiangchuan plexiglass Co. Ltd., φ300 mm×2 m) out-of-doors under a sunlight film (with a temperature of about 25□, a humidity of 60%-80%, and an illumination of 8000-20000 lux). Modified SM (see Table 2) was used. *Amoeba, Oxyrrhis* and ciliate contaminations were observed by microscope examination (Nikon fluorescent invert microscope Ti series). pH was adjusted to 10.0 with 1M ammonia. One hour later, $CO_2$ was aerated to saturation for 23 hour continuously (about pH 5.8). The result of microscope examination showed no *Amoeba* or *Oxyrrhis*, but a few inactive and immotile ciliates. Then air was sufficiently aerated. Twenty-four hours later, the algae could resume to grow. Compared with the situation of adjusting pH with NaOH, the algae clearly grew better in this case, because ammonia could be used as the nitrogen source for microalgae growth.

It should be understood by those skilled in the art that although the invention is is described in accordance with the exemplary embodiments, a variety of modifications can be made without deviating from the spirit and scope of the invention defined by the attached claims.

The invention claimed is:

1. A method for effectively controlling harmful organisms in the large-scale culture of microalgae, comprising:
   a. determining the harmful organism species causing contamination to the microalgae in culture, and the acid and alkali tolerance levels of said harmful organism species;
   b. adjusting the pH value of the microalgae culture system according to the different acid and alkali tolerance levels of the harmful organisms, and adjusting the pH value back to be suitable for the normal growth of the microalgae when the harmful organisms are determined to be killed or inhibited effectively,
   wherein when the harmful organism species is identified as alkali tolerant contamination, $CO_2$ is aerated into the microalgae culture system, and the pH value is adjusted back to be suitable for the normal growth of the microalgae by sufficiently aerating air or with alkalis when the harmful organisms are determined to be killed or inhibited effectively;
   when the harmful organism species is identified as acid tolerant contamination, the pH value of the microalgae culture system is raised up with alkalis to maintain a higher pH condition for the culture system, and adjusted back to be suitable for the growth of the microalgae when the harmful organisms are determined to be killed or inhibited effectively;

when the harmful organism species is identified as mixed contamination, the procedure below is followed depending on the species, harming rate and degree, as well as acid/alkali tolerance levels of the harmful organisms:

(1) in the case that alkali tolerant contamination is severer, the sample is first treated at a low pH for a while; after a relatively greater inhibiting and killing impact of this treatment is determined on the targeted harmful organisms, the harmful organisms with the opposite tolerance are treated at a high pH; the pH value is adjusted back to be suitable for the growth of the microalgae when the harmful organisms are determined to be killed or inhibited effectively; or (2) in the case that acid tolerant contamination is severer, the sample is first treated at a high pH for a while; after a relatively greater inhibiting and killing impact of this treatment is determined on the targeted harmful organisms, the harmful organisms with the opposite tolerance are treated at a low pH; the pH value is adjusted back to be suitable for the growth of the microalgae when the harmful organisms are determined to be killed or inhibited effectively.

2. The method according to claim 1, wherein the harmful organism with alkali tolerance that commonly exists in the microalgae culture is *Amoeba* sp.

3. The method according to claim 1, wherein the harmful organism with acid tolerance commonly exists in the microalgae culture is *Oxyrrhis* sp.

4. The method according to claim 1, wherein the harmful organism is selected from the mixed contamination of *Amoeba, Oxyrrhis*, ciliate, and other miscellaneous algae contamination.

5. The method according to claim 1, wherein the aeration of $CO_2$ maintains pH6.0-6.5, salinity is decreased by diluting the culture system with water when the contaminating organisms are determined to be killed or inhibited effectively, then air is sufficiently aerated.

6. The method according to claim 1, wherein the aeration of $CO_2$ allows saturation of $CO_2$, and the saturation period is determined according to contamination condition and microalgae's feature.

7. The method according to claim 6, wherein the saturation period is 1 hour.

8. The method according to claim 6, wherein the pH value in the saturation status is 5.6-5.7.

9. The method according to claim 1, wherein $CO_2$ is aerated periodically at an interval of 2 hours.

10. The method according to claim 1, wherein the pH value of the microalgae culture system is adjusted up to 8.0-11.0, 11.0-11.8 or 11.5-12.0 with alkalis.

11. The method according to claim 1, wherein the pH value is adjusted back to be suitable for the growth of the microalgae by sufficiently aerating air or if adjusted from a higher pH, by sufficiently aerating $CO_2$, and real-time detecting the pH value.

12. The method according to claim 1, wherein the pH value of the culture system is first raised up with alkalis, then $CO_2$ is aerated to be saturated; when the harmful organisms are determined to be in control by microscope examination, the pH value is adjusted back to be suitable for the growth of the microalgae by sufficiently aerating air.

13. The method according to claim 1, wherein the alkali is a conventional soluble non-heavy metal alkali.

14. The method according to claim 1, wherein the alkali is ammonia or NaOH.

* * * * *